United States Patent
Tanabe et al.

(10) Patent No.: US 10,130,843 B2
(45) Date of Patent: Nov. 20, 2018

(54) ELECTRONIC DEVICE, CONTROL PROGRAM, CONTROL METHOD, AND SYSTEM

(71) Applicant: KYOCERA Corporation, Kyoto-shi, Kyoto (JP)

(72) Inventors: Shigeki Tanabe, Yokohama (JP); Hideki Morita, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 335 days.

(21) Appl. No.: 14/891,672

(22) PCT Filed: May 16, 2014

(86) PCT No.: PCT/JP2014/063033
§ 371 (c)(1),
(2) Date: Nov. 16, 2015

(87) PCT Pub. No.: WO2014/185506
PCT Pub. Date: Nov. 20, 2014

(65) Prior Publication Data
US 2016/0101319 A1   Apr. 14, 2016

(30) Foreign Application Priority Data

May 17, 2013 (JP) .................. 2013-105442
Jun. 20, 2013 (JP) .................. 2013-129858
(Continued)

(51) Int. Cl.
*A63B 24/00* (2006.01)
*A61B 5/11* (2006.01)
*A61B 5/00* (2006.01)
*G01C 22/00* (2006.01)

(52) U.S. Cl.
CPC ........ *A63B 24/0062* (2013.01); *A61B 5/1118* (2013.01); *A61B 5/4866* (2013.01);
(Continued)

(58) Field of Classification Search
CPC .............................................. A63B 24/0062
(Continued)

(56) References Cited

U.S. PATENT DOCUMENTS

2006/0136173 A1* 6/2006 Case, Jr. et al. .............. 702/182
2011/0224925 A1   9/2011 Tsubata
2012/0316822 A1  12/2012 Barth et al.

FOREIGN PATENT DOCUMENTS

JP    2001-29323 A    2/2001
JP    2003-28967 A    1/2003
(Continued)

OTHER PUBLICATIONS

International Search Report dated Jul. 15, 2014, corresponding to International application No. PCT/JP2014/063033.
(Continued)

*Primary Examiner* — Thomas Hong
(74) *Attorney, Agent, or Firm* — Hauptman Ham, LLP

(57) ABSTRACT

An electronic device includes an acceleration sensor configured to detect an acceleration value, an atmospheric pressure sensor configured to detect an atmospheric pressure value, and a controller. The controller is configured to calculate the amount of activity or the number of steps based on the acceleration value detected by the acceleration sensor and the atmospheric pressure value detected by the atmospheric pressure sensor.

7 Claims, 6 Drawing Sheets

(30) Foreign Application Priority Data

Jun. 27, 2013 (JP) ................................ 2013-135051
Jun. 27, 2013 (JP) ................................ 2013-135052

(52) U.S. Cl.
CPC ........ *G01C 22/006* (2013.01); *A63B 2220/40* (2013.01); *A63B 2220/74* (2013.01)

(58) Field of Classification Search
USPC ........................................................ 434/255
See application file for complete search history.

(56) References Cited

FOREIGN PATENT DOCUMENTS

| | | |
|---|---|---|
| JP | 2003-156329 A | 5/2003 |
| JP | 2004-120688 A | 4/2004 |
| JP | 2008-524589 A | 7/2008 |
| JP | 2008-220517 A | 9/2008 |
| JP | 2009-200586 A | 9/2009 |
| JP | 2010-240158 A | 10/2010 |
| JP | 2010-253303 A | 11/2010 |
| JP | 2011-30643 A | 2/2011 |
| JP | 2011-215130 A | 10/2011 |
| WO | 2013/027918 A1 | 2/2013 |

OTHER PUBLICATIONS

Extended European Search Report in EP application No. 14798593.1, dated Dec. 14, 2016.
Office Action in JP application No. 2013-129858, dated Jun. 20, 2017.

\* cited by examiner

ELECTRONIC DEVICE, CONTROL PROGRAM, CONTROL METHOD, AND SYSTEM

CROSS-REFERENCE TO RELATED APPLICATION

This application is a National Stage of PCT international application Ser. No. PCT/JP2014/063033 filed on May 16, 2014 which designates the United States, incorporated herein by reference, and which is based upon and claims the benefit of priority from Japanese Patent Application No. 2013-105442 filed on May 17, 2013, and the benefit of priority from Japanese Patent Application No. 2013-129858 filed on Jun. 20, 2013, the benefit of priority from Japanese Patent Application No. 2013-135051 filed on Jun. 27, 2013, and the benefit of priority from Japanese Patent Application No. 2013-135052 filed on Jun. 27, 2013, the entire contents of which are incorporated herein by reference.

FIELD

The present disclosure relates to an electronic device and system having an acceleration sensor and a program and method for controlling the same.

BACKGROUND

Some pedometers can calculate calorie consumption (for example, see Japanese Patent Application Laid-open No. 2001-29323).

Some mobile devices have an atmospheric pressure sensor. A mobile device having an atmospheric pressure sensor is disclosed in Japanese Patent Application Laid-open No. 2003-28967, for example. In the mobile device disclosed in Japanese Patent Application Laid-open No. 2003-28967, an atmospheric pressure sensor is used for measuring an atmospheric pressure value.

Some electronic devices have a function of counting the number of steps based on a value detected by an acceleration sensor (for example, see Japanese Patent Application Laid-open No. 2004-120688).

CITATION LIST

Summary

An electronic device according to an embodiment comprises: an acceleration sensor configured to detect an acceleration value; an atmospheric pressure sensor configured to detect an atmospheric pressure value; and a controller configured to calculate an amount of activity or a number of steps based on the acceleration value detected by the acceleration sensor and the atmospheric pressure value detected by the atmospheric pressure sensor.

A control method of an embodiment comprises: detecting an acceleration using an acceleration sensor; detecting an atmospheric pressure value using an atmospheric pressure sensor; and calculating an amount of activity or a number of steps based on the detected acceleration and the detected atmospheric pressure value.

A computer program product according to an embodiment comprises a computer program product having computer instructions, stored on a non-transitory computer readable storage medium, for enabling a computer of an electronic device executing the computer instructions to perform operations comprising: detecting an acceleration using an acceleration sensor; detecting an atmospheric pressure value using an atmospheric pressure sensor; and calculating an amount of activity or a number of steps based on the detected acceleration and the detected atmospheric pressure value.

A system according to an embodiment comprises: an atmospheric pressure sensor configured to detect an atmospheric pressure; an acceleration sensor configured to detect an acceleration value; and a controller configured to count a number of steps based on the acceleration value detected by the acceleration sensor, wherein the controller mitigates a condition for counting the number of steps when it is determined based on the atmospheric pressure detected by the atmospheric pressure sensor that a variation in the atmospheric pressure in relation to the number of steps is larger than a predetermined value.

DESCRIPTION OF EMBODIMENTS

An embodiment of the present disclosure will be described in detail with reference to the drawings.

Figure 1:
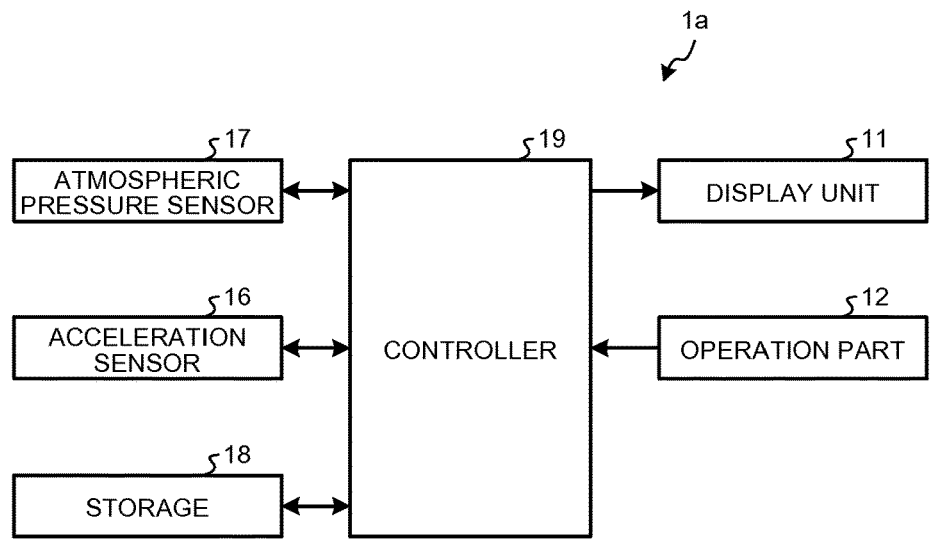
FIG. 1 is a block diagram illustrating a configuration of an electronic device according to an embodiment of some embodiments.

As illustrated in FIG. 1, an electronic device (mobile electronic device) 1a includes a display unit 11, an operation part 12, an atmospheric pressure sensor 17, an acceleration sensor 16, a storage 18, and a controller 19.

The display unit 11 is configured as a display device such as a liquid crystal display or an organic electro-luminescence panel. The display unit 11 displays characters, images, symbols, figures, or the like.

The operation part 12 includes a plurality of buttons and is operated by a user. The operation part 12 may include only one button.

The atmospheric pressure sensor 17 detects the pressure value of the atmosphere (atmospheric pressure value). Since there is a certain relation between an altitude from the ground and an atmospheric pressure, the controller 19 (described later) can calculate (obtain) an altitude from the atmospheric pressure value detected by the atmospheric pressure sensor 17.

The acceleration sensor 16 detects the direction and magnitude of an acceleration acting on the electronic device 1a and outputs a detection result to the controller 19. The acceleration sensor 16 is a 3G (3-dimensional) acceleration sensor that detects acceleration value values in X, Y, and Z-axis directions.

Although the acceleration sensor 16 is configured as a piezoresistive sensor and a capacitive sensor, for example, embodiments are not limited thereto. For example, the acceleration sensor 16 may be configured as a piezoelectric element (piezoelectric-type sensor), a heat-sensitive microelectromechanical systems (MEMS)-type sensor, a servo-type sensor in which a movable coil is displaced to return to its original position according to a feedback current, a strain gauge-type sensor that measures a strain occurring due to acceleration using a strain gauge, or other types of sensors.

The storage 18 is used when the controller 19 performs an arithmetic process, for example, and is configured as a memory or the like. The storage 18 stores metabolic equivalents (METs) used for calculating the amount of activity. The METs are the units of intensity expressing the intensity of physical activities and represent the metabolic rate during physical activity to the metabolic rate in a resting state. The larger the MET values, the higher the intensity of the physical activity. The storage 18 stores the MET value corresponding to a gradient (altitude difference). The storage 18 stores such a table (calculation formula) that the MET value increases as a rising gradient increases, for example. The storage 18 stores such a table (calculation formula) that the MET value decreases as a falling gradient increases, for example.

The storage 18 stores an acceleration pattern (starting acceleration pattern) used for determining that the user of the mobile electronic device 1a has started movement, an acceleration pattern (ending acceleration pattern) used for determining that the user of the mobile electronic device 1a has ended movement, an acceleration pattern (moving acceleration pattern) used for determining that the user of the mobile electronic device 1a is moving, and the like.

The controller 19 controls the entire mobile electronic device 1a and is configured using a central processing unit (CPU) or the like. The controller 19 determines the start and the end of movement based on an acceleration value. The controller 19 calculates the amount of activity based on an acceleration value and a difference between the atmospheric pressure values at the start and the end of movement.

In an embodiment, the controller 19 calculates a difference (atmospheric pressure difference) in the atmospheric pressure values at the start and the end of movement from the atmospheric pressure value detected by the atmospheric pressure sensor 17. For example, the controller 19 calculates the altitude difference at the start and the end of movement from the calculated atmospheric pressure difference by assuming that an atmospheric pressure difference of 1 [hPa (hectopascal)] corresponds to an altitude difference of 10 [m (meter)].

The controller 19 determines whether the movement of the mobile electronic device 1a has started or ended from the acceleration value detected by the acceleration sensor 16. The controller 19 compares the acceleration value detected by the acceleration sensor 16 with the acceleration pattern stored in the storage 18. The controller 19 compares the acceleration value detected by the acceleration sensor 16 with the starting acceleration pattern and determines that the user of the mobile electronic device 1a has started movement when the two acceleration values are identical or the difference falls within a predetermined range. When the controller 19 determines that the user of the mobile electronic device 1a has started movement, the atmospheric pressure sensor 17 detects an atmospheric pressure value at the start of movement and stores the atmospheric pressure value in the storage 18 as the atmospheric pressure value at the start of movement.

After the controller 19 determined that the user of the mobile electronic device 1a has started movement, the controller 19 compares the acceleration value detected by the acceleration sensor 16 with the moving acceleration pattern. When the two acceleration values are identical or the difference falls within a predetermined range, the controller 19 determines that the user of the mobile electronic device 1a is moving. When the two acceleration values are not identical or the difference is outside the predetermined range, the controller 19 determines that the user of the mobile electronic device 1a has ended movement. When the controller 19 determines that the user of the mobile electronic device 1a has ended movement, the atmospheric pressure sensor 17 detects an atmospheric pressure value at the end of movement and stores the atmospheric pressure value in the storage 18 as the atmospheric pressure value at the end of movement.

How the start and the end of movement are determined is not limited to the above-described embodiments.

Figure 2:
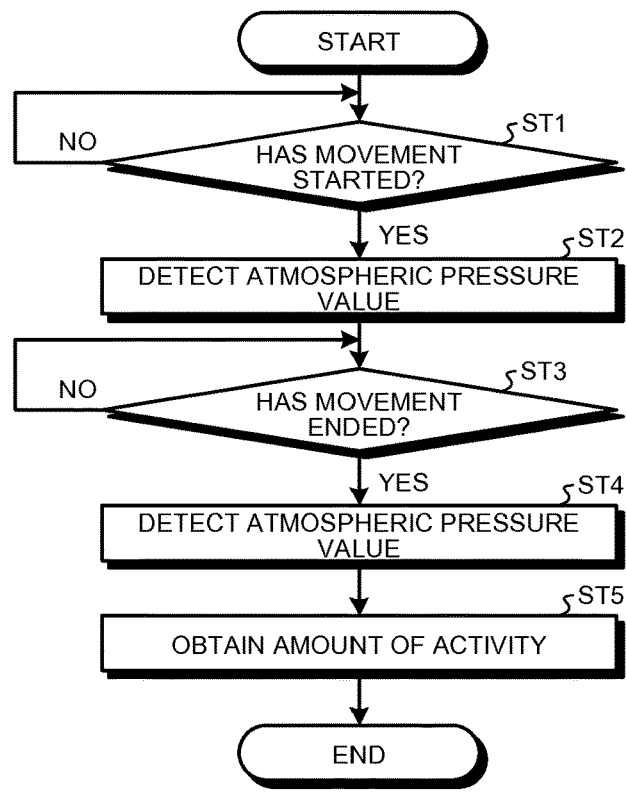
FIG. 2 is a flowchart illustrating a flow of an operation of an electronic device according to an embodiment of some embodiments.

Next, the flow of an operation of the mobile electronic device 1a will be described with reference to the flowchart illustrated in FIG. 2. The process of the flowchart illustrated in FIG. 2 starts when the mobile electronic device 1a is in a stopped state (for example, the user carrying the mobile electronic device 1a remains in a stopped state).

At Step ST1, the controller 19 determines whether the movement of the mobile electronic device 1a has started. When it is determined that the movement of the mobile electronic device 1a has started, the controller 19 detects an atmospheric pressure value at Step ST2. Subsequently, at Step ST3, the controller 19 determines whether the movement of the mobile electronic device 1a has ended. When it is determined that the movement of the mobile electronic device 1a has ended, the controller 19 detects an atmospheric pressure value at Step ST4. At Step ST5, the controller 19 calculates the amount of activity based on the acceleration value and the difference between the atmospheric pressure values at the start and the end of movement. In the operation of FIG. 2, it is assumed that the acceleration value is measured (detected).

The atmospheric pressure difference is used to specify the MET value stored in the storage 18. The acceleration value detected by the acceleration sensor 16 is used to determine the number of steps, the distance walked, the type of moving state, and the like when the amount of activity is calculated. Examples of the type of moving state include, but are not limited to, walking, traveling, and bicycle-riding.

Then, when the moving state of the mobile electronic device 1a is determined to be bicycle-riding based on the acceleration value detected by the acceleration sensor 16 and a bicycle type is set to power-assisted (user's setting), the controller 19 calculates the amount of activity without based on an atmospheric pressure. This is because the MET value which is a parameter for calculating the amount of activity when the user moves on a bumpy road while riding a power-assisted bicycle is different from that when the user moves while riding a normal bicycle (a bicycle which is not power-assisted). Since the amount of activity of a user having moved along a flat road is not much different from that of a user having climbed a slope while riding a power-assisted bicycle, when the bicycle type is set to power-assisted (user's setting), it may be ideal to calculate the amount of activity without based on an atmospheric pressure. When the MET value for a power-assisted bicycle is stored, the amount of activity may be calculated using the MET value.

Another embodiment of the present disclosure will be described in detail with reference to the drawings. In the following description, a mobile electronic device 1b will be described as an example of an electronic device (mobile electronic device). The mobile electronic device 1b is a mobile phone, for example.

Figure 3:
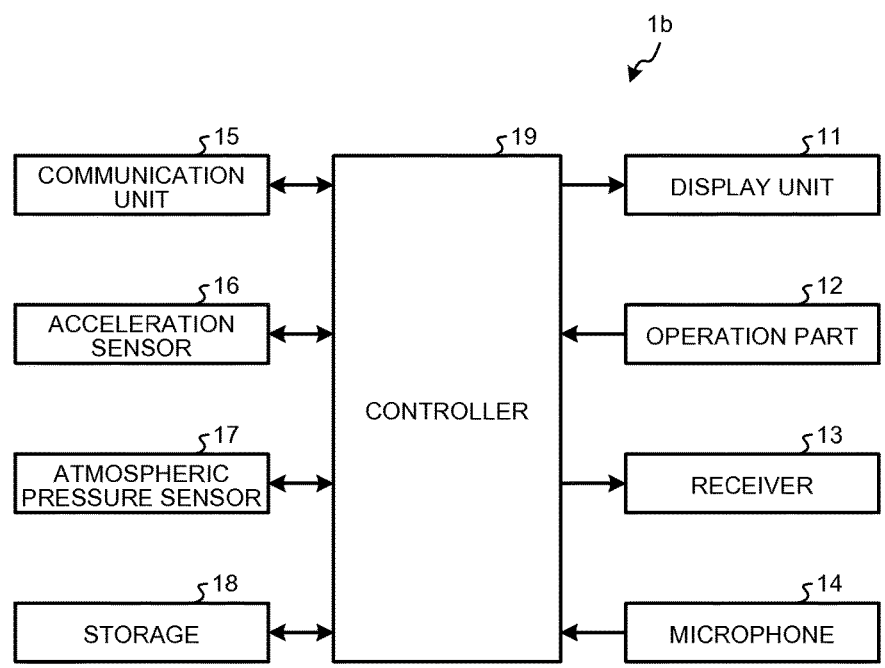
FIG. 3 is a block diagram illustrating a configuration of an electronic device according to an embodiment of some embodiments.

As illustrated in FIG. 3, the mobile electronic device 1b includes a display unit 11, an operation part 12, a receiver 13, a microphone 14, a communication unit 15, an acceleration sensor 16, an atmospheric pressure sensor 17, a storage 18, and a controller 19.

The display unit 11 is a portion that displays information. The display unit 11 is configured as a display device. Examples of a display device include, but are not limited to, a liquid crystal display and an organic electro-luminescence panel. The display unit 11 displays characters, images, symbols, figures, or the like.

The operation part 12 is a portion that receives an operation made by a user. The mobile electronic device 1b of an embodiment includes various operation buttons, switches, or a touch screen as the operation part 12. When a touch screen is included as the operation part 12, a touch screen display integrated with the display unit 11 may be included.

The receiver 13 converts an audio signal transmitted from the controller 19 to audible sound and outputs the audible sound.

The communication unit 15 includes an antenna and an RF circuit unit. The communication unit 15 performs communication according to communication schemes corresponding to a plurality of wireless communication standards. The communication unit 15 enables communication according to a wireless LAN system or cellular phone communication standards such as 2G, 3G, and 4G. The communication unit 15 enables communication according to a wireless communication system conforming to IEEE 802.11, which is a wireless LAN system, such as a Wi-Fi (registered trademark) wireless communication system. The communication unit 15 may perform communication according to a WiMAX (registered trademark) wireless communication system. A plurality of antennas and RF circuit units are provided so as to correspond to a plurality of communication schemes. In an embodiment, it is assumed that the communication unit 15 performs communication according to Wi-Fi.

The acceleration sensor 16 detects the direction and the magnitude of the acceleration acting on the mobile electronic device 1b and outputs a detection result to the controller 19 as an acceleration signal. The controller 19 receives the acceleration signal output by the acceleration sensor 16. In an embodiment, a 3G (3-dimensional) acceleration sensor that detects acceleration values in X, Y, and Z-axis directions is used as the acceleration sensor 16.

Although the acceleration sensor 16 is configured as a piezoresistive sensor and a capacitive sensor, for example, embodiments are not limited thereto. For example, the acceleration sensor 16 may be configured as a piezoelectric element (piezoelectric-type sensor), a heat-sensitive microelectromechanical systems (MEMS)-type sensor, a servo-type sensor in which a movable coil is displaced to return to its original position according to a feedback current, a strain gauge-type sensor that measures a strain occurring due to acceleration using a strain gauge, or other types of sensors.

The atmospheric pressure sensor 17 detects the magnitude of an atmospheric pressure acting on the mobile electronic device 1b and outputs a detection result to the controller 19 as an atmospheric pressure signal. The controller 19 receives the atmospheric pressure signal output by the atmospheric pressure sensor 17.

The storage 18 is used when the controller 19 performs an arithmetic process, for example, and is configured as a memory or the like. The storage 18 stores one or a plurality of applications that operates inside the mobile electronic device 1b. The storage 18 may serve as a removable external memory.

The controller 19 controls the entire mobile electronic device 1b and is configured using a central processing unit (CPU), a micro-processing unit (MPU), or the like.

Hereinafter, how the detection result obtained by the acceleration sensor 16 is processed by the controller 19 will be described.

Figure 4:
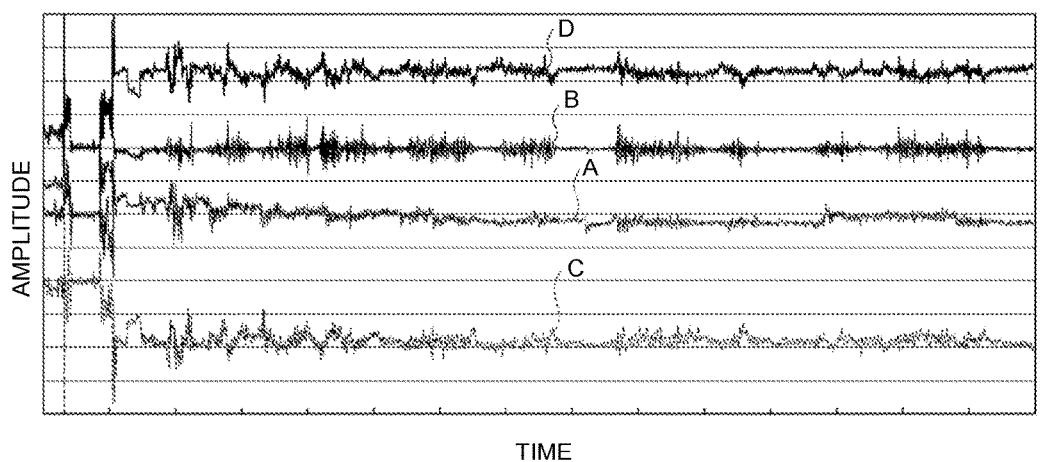
FIG. 4 is a diagram schematically illustrating detection results obtained by an acceleration sensor according to an embodiment of some embodiments.

As illustrated in FIG. 4, the controller 19 receives an X-axis acceleration signal (A in FIG. 4), a Y-axis acceleration signal (B in FIG. 4), a Z-axis acceleration signal (C in FIG. 4), and a vector value (D in FIG. 4) obtained by combining the three-axis acceleration signals as the detection result obtained by the acceleration sensor 16. The controller 19 logs the combined vector value. The controller 19 analyzes the logged data to determine an acceleration state of the mobile electronic device 1b. The logged combined vector is stored in the storage 18.

The controller 19 uses an acceleration pattern when determining the acceleration state of the mobile electronic device 1b. The acceleration pattern is stored in advance in the storage 18, for example. The acceleration pattern is correlated with a stopping state and a plurality of moving states of the user. The acceleration pattern is measured and extracted in advance by the acceleration sensor 16 detecting a characteristic acceleration pattern in the stopping state and the plurality of moving states. Examples of the acceleration pattern include, but are not limited to, a case in which the user of the mobile electronic device 1b is in a stopping state, a case in which the user of the mobile electronic device 1b is in an acceleration state of moving by walking, a case in which the user of the mobile electronic device 1b is in an acceleration state of moving while riding a bicycle, and a case in which the user of the mobile electronic device 1b is in an acceleration state of moving by a vehicle such as an automobile or a train.

In an embodiment, for example, the acceleration pattern is stored in advance in the storage 18 in correlation with the stopping state and the plurality of moving states. The acceleration pattern is stored so as to correspond to the logged data of the combined vector value. The controller 19 determines the acceleration state of the mobile electronic device 1b by comparing the logged data of the combined vector value with the acceleration pattern.

The controller 19 may determine that the mobile electronic device is in a stopping state when the acceleration value detected by the acceleration sensor 16 is smaller than a predetermined value rather than using the acceleration pattern corresponding to the stopping state. The controller 19 may determine that the mobile electronic device is in a stopping state when the logged data of the combined vector value is not identical to any one of the plurality of moving states rather than using the acceleration pattern corresponding to the stopping state.

Hereinafter, how the detection result obtained by the atmospheric pressure sensor 17 is processed by the controller 19 will be described. The detection result obtained by the atmospheric pressure sensor 17 is processed by the controller 19 when the controller 19 executes a control program. The controller 19 realizes the following control method by executing the control program.

The controller 19 receives the atmospheric pressure signal as the detection result obtained by the atmospheric pressure sensor 17. The controller 19 logs the atmospheric pressure signal. The controller 19 analyzes a change in the atmospheric pressure signal to determine an altitudinal change of the mobile electronic device 1b. The logged atmospheric pressure signal is stored in the storage 18.

The controller 19 can process the change in the atmospheric pressure signal output by the atmospheric pressure sensor 17 as an atmospheric pressure change resulting from the altitudinal change. For example, the controller 19 determines by assuming that an atmospheric pressure change of 1 [hPa (hectopascal)] corresponds to an altitudinal change of 10 [m (meter)].

The controller 19 uses the atmospheric pressure signal as a reference value when determining that a change in the atmospheric pressure signal results from a change in atmospheric pressure, which results from an altitudinal change. The controller 19 processes a difference from the reference value of the atmospheric pressure signal as an atmospheric pressure change resulting from an altitudinal change. In other words, the controller 19 converts a difference from the reference value of the atmospheric pressure signal to an altitudinal change. The controller 19 can flexibly cope with a change in atmospheric pressure by changing the reference value of the atmospheric pressure signal used when processing the change in atmospheric pressure signal as an altitudinal change. When the change in atmospheric pressure signal is converted to an altitudinal change, the controller 19 sequentially adds the converted altitudinal change as a difference from the present height. When the converted altitudinal change is sequentially added as the difference from the present height, the controller 19 processes a height to which the altitudinal change is added as the present height. The controller 19 can flexibly cope with the changes in altitude even when the mobile electronic device moves up and down by sequentially adding the converted altitudinal change as the difference from the present height.

The controller 19 stores the changes in the altitudinal change in the storage 18 as a height difference log. The height difference log stored in the storage 18 starts from a new reference height in each unit period. By starting the height difference log from a new reference height in each unit period, the mobile electronic device 1b can suppress accumulation of errors in the altitudinal change. Examples of the unit period include, but are not limited to, 12 hours, one day, and one week. This unit period is preferably the same as the unit of displaying the height difference log as a series of data.

When there is a change in the atmospheric pressure signal detected by the atmospheric pressure sensor 17, the controller 19 determines whether the change in the atmospheric pressure signal is an atmospheric pressure change resulting from an altitudinal change or a change in atmospheric pressure.

Figure 5A:
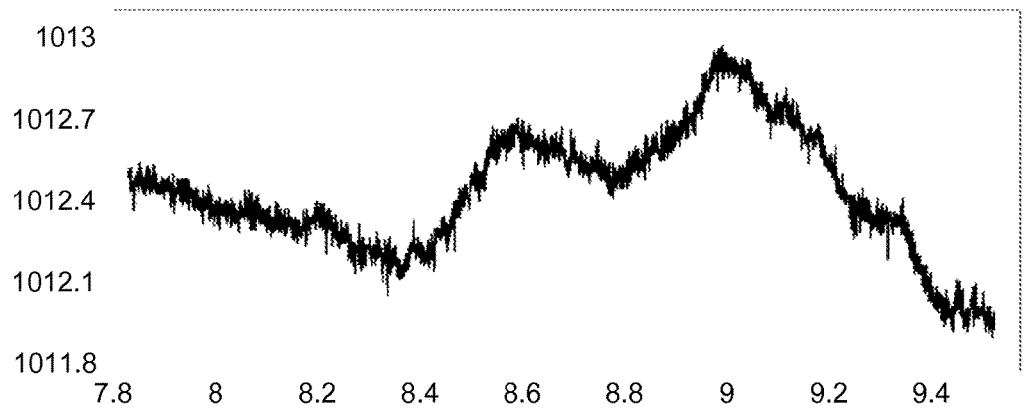
FIG. 5A is a diagram schematically illustrating detection results obtained by an atmospheric pressure sensor according to an embodiment of some embodiments.
Figure 5B:
FIG. 5B is a diagram schematically illustrating detection results obtained by an atmospheric pressure sensor according to an embodiment of some embodiments.
Figure 5C:
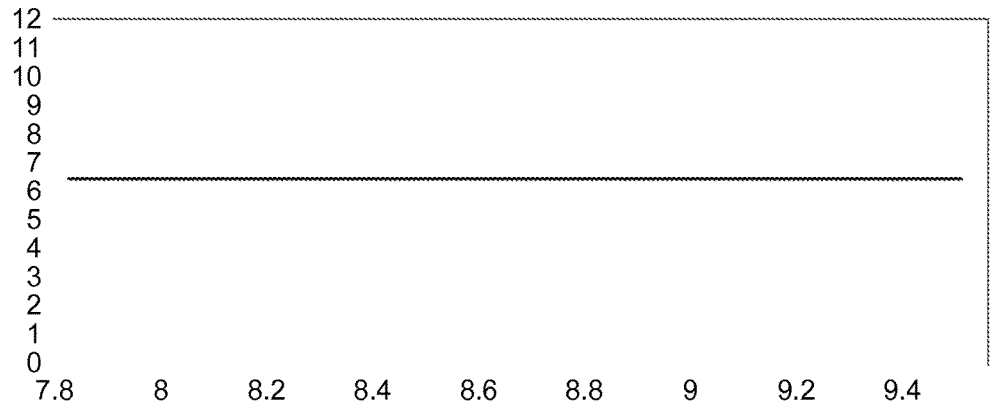
FIG. 5C is a diagram schematically illustrating detection results obtained by an atmospheric pressure sensor according to an embodiment of some embodiments.

FIGS. 5A to 5C are diagrams schematically illustrating a detection result obtained by an atmospheric pressure sensor. FIG. 5A illustrates a change with time in the atmospheric pressure value detected by the atmospheric pressure sensor 17. In FIG. 5A, the horizontal axis represents time and the vertical axis represents atmospheric pressure value. The unit of time is second (sec) and the unit of atmospheric pressure signal is hectopascal (hPa). FIG. 5B illustrates an altitudinal change when the controller 19 processes the change with time in the atmospheric pressure illustrated in FIG. 5A as an atmospheric pressure change resulting from an altitudinal change. In FIG. 5B, the horizontal axis represents time and the vertical axis represents altitude. The unit of time is second (sec) and the unit of altitude is meter (m). FIG. 5C illustrates an altitudinal change when the controller 19 converts the change with time in the atmospheric pressure illustrated in FIG. 5A to an atmospheric pressure change resulting from the change in atmospheric pressure. In FIG. 5C, the horizontal axis represents time and the vertical axis represents altitude similarly to FIG. 5B. The unit of time is second (sec) and the unit of altitude is meter (m). The mobile electronic device 1b determines whether the change with time in the atmospheric pressure value detected by the atmospheric pressure sensor 17 is an atmospheric pressure change resulting from an altitudinal change or the change in atmospheric pressure.

The controller 19 refers to an acceleration state when analyzing the change in the atmospheric pressure signal. In other words, the controller 19 analyzes the change in the atmospheric pressure signal based on the acceleration signal detected by the acceleration sensor 16. The controller 19 determines whether the change in the atmospheric pressure signal results from an altitudinal change or an atmospheric pressure change based on the acceleration signal detected by the acceleration sensor 16.

When it is determined that the mobile electronic device 1b is in a stopping state based on the acceleration state, the controller 19 determines that the change in the atmospheric pressure signal detected by the atmospheric pressure sensor 17 results from an atmospheric pressure change. When it is determined that the mobile electronic device 1b is in a moving state based on the acceleration state, the controller 19 determines that the change in the atmospheric pressure signal detected by the atmospheric pressure sensor 17 results from an altitudinal change. Since the controller 19 performs such control, the mobile electronic device 1b of an embodiment can ideally determine whether the change in the atmospheric pressure signal results from a movement.

The controller 19 changes an acquisition cycle at which the atmospheric pressure sensor 17 acquires an atmospheric pressure signal based on the acceleration state. When it is determined that the acceleration state is a moving state, the controller 19 changes the acquisition cycle at which the atmospheric pressure sensor 17 acquires the atmospheric pressure signal according to the determined moving state. The faster the moving velocity corresponding to the determined moving state, the shorter the acquisition cycle set by the controller 19, at which the atmospheric pressure sensor 17 acquires the atmospheric pressure signal. For example, the controller 19 sets the acquisition cycle when the acceleration state indicates that the user is running to be shorter than the acquisition cycle when the acceleration state indicates that the user is walking. For example, the controller 19 sets the acquisition cycle when the acceleration state indicates that the user is moving while riding a bicycle to be shorter than the acquisition cycle when the acceleration state indicates that the user is running. For example, the controller 19 sets the acquisition cycle when the acceleration state indicates that the user is moving by a vehicle such as an automobile or a train to be shorter than the acquisition cycle when the acceleration state indicates that the user is moving while riding a bicycle. The controller 19 sets the acquisition cycle when the acceleration state indicates that the user is in the stopping state to be longer than the acquisition cycle when the acceleration state indicates that the user is in the moving state. When the acceleration state indicates that the user is in the stopping state, the controller 19 may control the atmospheric pressure sensor 17 so as not to acquire an atmospheric pressure signal. The atmospheric pressure sensor 17 can be controlled so as not to acquire the atmospheric pressure signal when a trigger signal that triggers acquisition of an atmospheric pressure signal is not input to the atmospheric pressure sensor 17 or when an electric power is not supplied to the atmospheric pressure sensor 17.

In the above-described configuration, although a configuration in which the controller 19 changes the acquisition cycle at which the atmospheric pressure sensor 17 acquires the atmospheric pressure signal based on the acceleration state has been employed, embodiments are not limited thereto.

The controller 19 may change an output cycle at which the atmospheric pressure sensor 17 outputs an atmospheric pressure signal based on the acceleration state. When the controller 19 changes the output cycle, the output cycle may be changed according to the determined moving state. The controller 19 may change the output cycle so that the output cycle when the user is in the stopping state is longer than the output cycle when the user is in the moving state. The controller 19 may change the output cycle so that the controller 19 controls the atmospheric pressure sensor 17 so as not to output the atmospheric pressure signal when the acceleration state indicates that the user is in the stopping state. The atmospheric pressure sensor 17 can be controlled so as not to output the atmospheric pressure signal when a trigger signal that triggers outputting of the atmospheric pressure signal is not input to the atmospheric pressure sensor 17 or when an electric power is not supplied to the atmospheric pressure sensor 17.

The controller 19 may change a reception cycle at which the atmospheric pressure signal output by the atmospheric pressure sensor 17 is received based on the acceleration state. The controller 19 may change the reception cycle according to the determined moving state. The controller 19 may change the reception cycle so that the reception cycle when the user is in the stopping state is longer than the reception cycle when the user is in the moving state. The controller 19 may change the reception cycle so that the controller 19 does not receive the atmospheric pressure signal output by the atmospheric pressure sensor 17 when the acceleration state indicates that the user is in the stopping state.

The controller 19 may change a determination cycle at which a change in the atmospheric pressure signal detected by the atmospheric pressure sensor 17 is determined based on the acceleration state. The controller 19 may change the determination cycle according to the determined moving state. The controller 19 may change the determination cycle so that the determination cycle when the user is in the stopping state is longer than the determination cycle when the user is in the moving state. The controller 19 may change the determination cycle so that the controller 19 does not determine the change in the atmospheric pressure signal output by the atmospheric pressure sensor 17 when the acceleration state indicates that the user is in the stopping state.

Since the controller 19 changes any one of the acquisition cycle, the output cycle, the reception cycle, and the determination cycle, the mobile electronic device 1b can determine an altitudinal change at an ideal cycle while appropriately determining whether the change in the atmospheric pressure signal results from an altitudinal change. When the controller 19 changes any one of the acquisition cycle, the output cycle, the reception cycle, and the determination cycle, the mobile electronic device 1b can reduce power consumption.

The controller 19 receives an acceleration signal as the detection result obtained by the acceleration sensor 16. The controller 19 logs the acceleration signal. The logged acceleration signal is stored in the storage 18. The controller 19 analyzes a change in the acceleration signal to determine a vibration amplitude of the acceleration signal. A peak-to-peak value in a unit period is used as the vibration amplitude of the acceleration signal. The unit period may be several seconds, for example. The controller 19 can flexibly cope with a change in DC component of an acceleration value by using the peak-to-peak value as the vibration amplitude of the acceleration signal.

The controller 19 changes a period in which it is determined that the change in the atmospheric pressure signal detected by the atmospheric pressure sensor 17 results from an altitudinal change based on the vibration amplitude of the acceleration signal detected by the acceleration sensor 16. When the vibration amplitude of the acceleration signal detected by the acceleration sensor 16 is larger than a first value, the controller 19 determines that the change in the atmospheric pressure signal detected in a first period in which a first time passes results from an altitudinal change. When a relatively large change in the acceleration signal occurring when the user starts moving is detected, the controller 19 processes the change in the atmospheric pressure signal in a predetermined period after the change in the acceleration signal is detected as an altitudinal change.

When the vibration amplitude of the acceleration signal detected by the acceleration sensor 16 is larger than a second value, the controller 19 determines that the change in the atmospheric pressure signal detected by the atmospheric pressure sensor 17 results from an altitudinal change. The controller 19 determines that the change in the atmospheric pressure signal detected by the atmospheric pressure sensor 17 results from an altitudinal change in the period in which the vibration amplitude of the acceleration signal is larger than the second value. The second value is smaller than the first value. When such a change in the acceleration signal that occurs continuously with movement of the user is detected, the controller 19 processes the change in the atmospheric pressure signal when the change in the acceleration signal is detected as an altitudinal change.

The controller 19 of an embodiment processes the change in the atmospheric pressure signal after it is determined that the change in the atmospheric pressure signal is an atmospheric pressure change resulting from an altitudinal change as an atmospheric pressure change that results from an altitudinal change. In the mobile electronic device 1b, it is possible to simplify the control since the controller 19 processes the change in signals obtained after it is determined that the change in the atmospheric pressure signal is an atmospheric pressure change resulting from an altitudinal change as an atmospheric pressure change resulting from an altitudinal change. When the control is simplified, the mobile electronic device 1b can realize its function with a simple configuration.

Figure 6:
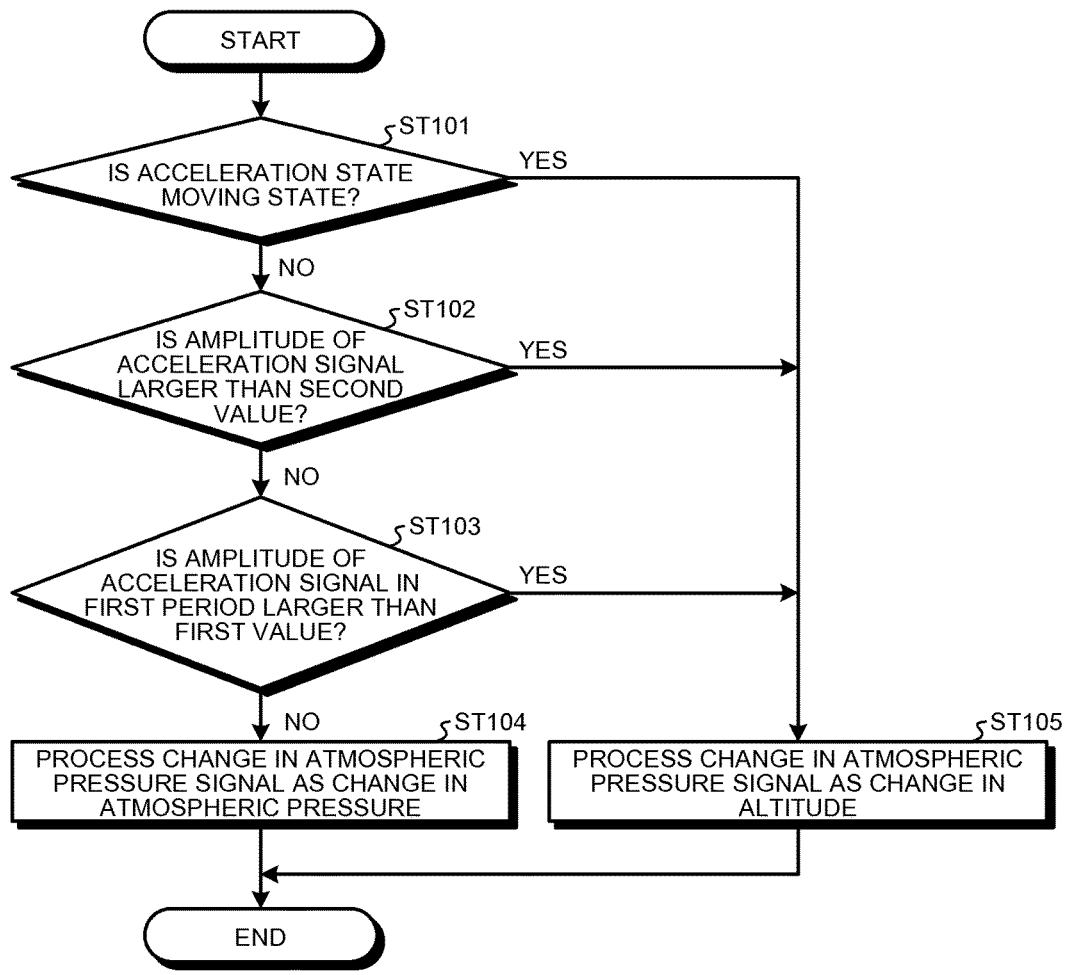
FIG. 6 is a flowchart provided for description of a flow of an operation of an electronic device according to an embodiment of some embodiments.

The flow of an operation of the mobile electronic device 1b will be described with reference to the flowchart illustrated in FIG. 6. In following embodiments, it is assumed that the acceleration state is determined in real time. The mobile electronic device 1b is not limited to this one embodiment but may determine the acceleration state at predetermined time intervals.

At Step ST101, the controller 19 determines whether the acceleration state is a moving state based on the detection result obtained by the acceleration sensor 16. The controller 19 proceeds to Step ST105 when a determination result of YES is obtained. The controller 19 proceeds to Step ST102 when a determination result of NO is obtained. At Step ST101, the controller 19 changes the step to proceed to by determining whether the acceleration state indicated by the acceleration signal detected by the acceleration sensor 16 is a stopping state or a moving state.

At Step ST102, the controller 19 determines whether the amplitude of the acceleration signal detected by the acceleration sensor 16 is larger than a second value. The controller 19 proceeds to Step ST105 when a determination result of YES is obtained. The controller 19 proceeds to Step ST103 when a determination result of NO is obtained.

At Step ST103, the controller 19 determines whether the amplitude of the acceleration signal detected by the acceleration sensor 16 is larger than a first value in a first period. The controller 19 proceeds to Step ST105 when a determination result of YES is obtained. The controller 19 proceeds to Step ST104 when a determination result of NO is obtained. At Step ST103, the controller 19 changes the step to proceed to by determining whether the first period in which a first time passes has elapsed after it was determined that the amplitude of the acceleration signal is larger than the first value.

At Step ST104, the controller 19 processes the change in the atmospheric pressure signal detected by the atmospheric pressure sensor 17 as the change in atmospheric pressure. When the process of Step 104 ends, the controller 19 completes the process of this control flow. At Step ST104, the controller 19 stores the value of the atmospheric pressure signal detected by the atmospheric pressure sensor 17 in the storage 18 as the present atmospheric pressure value. The value stored in the storage 18 as the present atmospheric pressure value is used as a reference when processing the change in the atmospheric pressure signal as a change resulting from an altitudinal change.

At Step ST105, the controller 19 processes the change in the atmospheric pressure signal detected by the atmospheric pressure sensor 17 as a change resulting from an altitudinal change. When the process of Step 105 ends, the controller 19 completes the process of this control flow.

The controller 19 of an embodiment determines whether the change in the atmospheric pressure signal is the change in atmospheric pressure or an atmospheric pressure change resulting from an altitudinal change by repeating this control flow. The controller 19 can reflect the change in the atmospheric pressure signal as an altitudinal change by repeating this control flow.

This control flow may omit two or smaller steps as long as the control flow includes at least one of Steps ST101 to ST103.

In the control flow, Steps ST101, ST102, and ST103 were performed sequentially. The controller 19 may be configured to execute Steps ST101 to ST103 simultaneously and to process the change in the atmospheric pressure signal as the change resulting from the altitudinal change when a determination result of YES is obtained in at least one of the steps.

While an embodiment of the present disclosure has been described, the present disclosure is not limited to the above-described one embodiment. The advantageous effects of the present disclosure are not limited to those described in embodiments.

In the above-described one embodiment, although it is determined that the acceleration state of the mobile electronic device 1b is any one of the stopping state and the plurality of moving states based on the acceleration value detected by the acceleration sensor 16, the embodiments are not limited thereto. For example, the mobile electronic device 1b may measure the position of the mobile electronic device 1b using a global positioning system (GPS) and may determine whether the mobile electronic device 1b is in any one of the stopping state and the plurality of moving states based on a displacement amount per unit time (predetermined period) of the mobile electronic device 1b.

In the above-described one embodiment, although the controller 19 processes the change in the atmospheric pressure signal after it was determined that the change in the atmospheric pressure signal is an atmospheric pressure change resulting from the altitudinal change as an atmospheric pressure change resulting from the altitudinal change, the embodiments are not limited thereto. The controller 19 may process the change in the atmospheric pressure signal when it is determined that the change in the atmospheric pressure signal is an atmospheric pressure change resulting from the altitudinal change as an atmospheric pressure change resulting from the altitudinal change. The mobile electronic device 1b can reflect the altitudinal change more accurately since the controller 19 processes the change in the atmospheric pressure signal when it is determined that the change in the atmospheric pressure signal is an atmospheric pressure change resulting from the altitudinal change as an atmospheric pressure change resulting from the altitudinal change. The mobile electronic device 1b may process the data logged to the storage 18 and may include a buffer that temporarily stores the change in the atmospheric pressure signal so that the controller 19 can process the change in the atmospheric pressure signal when it is determined that the change in the atmospheric pressure signal is an atmospheric pressure change resulting from the altitudinal change as an atmospheric pressure change resulting from the altitudinal change.

Figure 7:
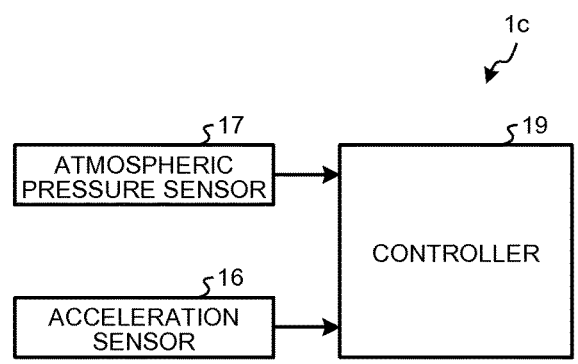
FIG. 7 is a block diagram illustrating a configuration of an electronic device according to an embodiment of some embodiments.

Hereinafter, another embodiment of an electronic device (mobile electronic device) according to the present disclosure will be described. FIG. 7 is a block diagram illustrating a configuration of an electronic device 1c according to an embodiment.

Examples of the electronic device 1c include, but are not limited to, a mobile phone, a tablet computer, a pedometer, and a mobile game console.

The electronic device 1c includes an atmospheric pressure sensor 17, an acceleration sensor 16, and a controller 19.

The atmospheric pressure sensor 17 detects an atmospheric pressure value. The electronic device 1c can detect an altitude or an altitudinal change since the atmospheric pressure sensor 17 detects the atmospheric pressure value.

The acceleration sensor 16 detects an acceleration value. The acceleration sensor 16 detects acceleration values in X, Y, and Z-axes.

The controller 19 determines a resting state (stopping state) or the type of a moving state based on the acceleration value detected by the acceleration sensor 16. The controller 19 may preferably determine a state in which a user is walking, a state in which a user is traveling, and a state in which a user is moving while riding a moving vehicle as the type of the moving state.

The controller 19 detects the acceleration value detected by the acceleration sensor 16. The controller 19 receives an X-axis acceleration value (A in FIG. 4), a Y-axis acceleration value (B in FIG. 4), a Z-axis acceleration value (C in FIG. 4), and a vector value (D in FIG. 4) obtained by combining the acceleration values from the acceleration sensor 16. Examples of a case in which the acceleration value changes include, but are not limited to, a case in which the user is walking, a case in which the user is riding on a vehicle, and a case in which the user is operating the electronic device 1*c*. Thus, the controller 19 identifies the present case from the above-mentioned cases based on the vector value obtained by combining the respective acceleration values, for example. For example, the amplitude (vibration amount) of an acceleration and a vibration cycle are different from case to case, including a case in which a person is walking, a case in which a person is running (traveling), a case in which a person is riding a bicycle, a case in which a person is riding on an automobile, a case in which a person is riding on a train (for example, a conventional train line), a case in which a person is riding on a bullet train, and a case in which the electronic device 1*c* is operated. Thus, the controller 19 sets a threshold of an amplitude and a threshold of a vibration cycle in order to detect the respective cases. When a vehicle is identified based on an acceleration value in a short period, the controller 19 may make a determination error due to a temporarily vibration or the like of the electronic device 1*c*. Thus, the controller 19 acquires an acceleration value in a predetermined period and identifies the type of a vehicle corresponding to the conditions of the amplitude and the vibration cycle when the condition is satisfied successively in the predetermined period. In this way, the controller 19 can identify the type of the moving state.

When there is no or approximately no change in the acceleration value, the controller 19 determines that the user is in the resting state.

The controller 19 calculates an amount of physical activity based on the determination result and the atmospheric pressure value detected by the atmospheric pressure sensor 17. Examples of the amount of physical activity include, but are not limited to, the amount of exercise (MET value) and the amount of energy consumption (cal). For example, the amount of energy consumption can be calculated according to the following equation (1) using the MET value.

$$\text{Amount of Energy Consumption (kcal)} = 1.05 \times \text{MET} \times \text{Period} \times \text{Weight (kg)} \quad (1)$$

The controller 19 changes the MET value according to an altitudinal change obtained based on the atmospheric pressure value detected by the atmospheric pressure sensor 17. The controller 19 updates the MET value every 10 steps, for example, when the type of the moving state determined based on the detection result obtained by the acceleration sensor 16 is a state in which a person is running. That is, the controller 19 acquires an altitude every 10 steps based on the detection result obtained by the atmospheric pressure sensor 17. The controller 19 calculates a gradient of the road surface based on a step length of a person and the change in the altitude every 10 steps. The step length of a person is registered in advance by a user, for example. The controller 19 changes the MET value based on the calculated gradient. For example, the controller 19 sets the MET value to 6.5 when the gradient is between 1 and 3%, the MET value to 7.0 when the gradient is between 3 and 6%, the MET value to 5.5 when the gradient is between −1 and −3%, and the MET value to 5.0 when the gradient is between −3 and −6%. The MET value is 6.0 when a person is running on a level ground at a speed of 6.4 [km/h (kilometers per hour)].

The controller 19 updates the MET value every 10 steps, for example, when the type of the moving state determined based on the detection result obtained by the acceleration sensor 16 is a case in which a person is walking. That is, the controller 19 acquires the altitude every 10 steps based on the detection result obtained by the atmospheric pressure sensor 17. The controller 19 calculates the gradient of a road surface based on the step length of a person and the change in the altitude every 10 steps. The step length of a person is registered in advance by a user, for example. The controller 19 changes the MET value based on the calculated gradient. When the user stops walking in the number of steps (for example, seven steps) smaller than 10 steps, the gradient of the road surface is calculated based on an altitudinal change corresponding to seven steps.

The controller 19 updates the MET value every 10 seconds when the type of the moving state determined based on the detection result obtained by the acceleration sensor 16 is a state in which a person is riding a bicycle. That is, the controller 19 acquires an altitude every 10 seconds based on the detection result obtained by the atmospheric pressure sensor 17. The controller 19 calculates a gradient of the road surface based on the distance traveled and the change in the altitude every 10 seconds. The distance traveled is obtained based on a preset velocity (for example, 8.9 [km/h]) and a period (10 seconds), for example. The controller 19 changes the MET value based on the calculated gradient.

The controller 19 changes a cycle (hereinafter sometimes referred to as a "detection cycle") at which the atmospheric pressure sensor 17 detects the atmospheric pressure value based on the determined type of the moving state. The controller 19 sets the detection cycle of the atmospheric pressure sensor 17 to one seconds, for example, when it is determined that a person is walking. The controller 19 sets the detection cycle of the atmospheric pressure sensor 17 to 0.5 seconds, for example, when it is determined that a person is running. The controller 19 sets the detection cycle of the atmospheric pressure sensor 17 to 0.1 seconds, for example, when it is determined that a person is riding a bicycle.

The atmospheric pressure sensor 17 consumes electric power when detecting the atmospheric pressure value. On the other hand, since the change in altitude when the moving velocity of the electronic device 1*c* is slow is smaller than that when the moving velocity is fast, the atmospheric pressure sensor 17 does not need to detect the atmospheric pressure value frequently. Thus, power consumption is suppressed by setting the detection cycle of the atmospheric pressure sensor 17 when the moving velocity is slow to be longer than that when the moving velocity is fast.

Thus, the electronic device 1*c* can provide a plurality of functions since it is possible to determine the resting state or the type of the moving state and to calculate the amount of energy consumption, for example. Since the electronic device 1*c* changes the detection cycle of the atmospheric pressure sensor 17 according to the type of the moving state, it is possible to suppress power consumption.

When it is determined that the user is in the resting state, the controller 19 may preferably stop driving the atmospheric pressure sensor 17. When the detection result obtained by the acceleration sensor 16 indicates that the user is in the resting state, the altitude is less likely to change. When the user is in the resting state, exercise-based energy is less likely to be consumed. Thus, the controller 19 stops the driving of the atmospheric pressure sensor 17 by not transmitting a signal for detecting the atmospheric pressure value to the atmospheric pressure sensor 17.

In this way, the electronic device 1c can suppress the power consumed by the atmospheric pressure sensor.

When it is determined that the user is in the resting state, the controller 19 may preferably cause the atmospheric pressure sensor 17 to stop the atmospheric pressure detection operation. When the detection result obtained by the acceleration sensor 16 indicates that the user is in the resting state, the altitude is less likely to change. When the user is in the resting state, exercise-based energy is less likely to be consumed. Thus, when it is determined that the user is in the resting state, the atmospheric pressure sensor 17 stops the atmospheric pressure detection operation.

After the type of the moving state is determined, the controller 19 may preferably calculate an average moving velocity. Further, the controller 19 may preferably change the cycle at which the atmospheric pressure sensor 17 detects the atmospheric pressure value based on the type of the moving state and the average moving velocity. When a person is walking or a person is running, the controller 19 can count the number of steps based on the detection result obtained by the acceleration sensor 16. The controller 19 can obtain the average moving velocity based on the counted number of steps, a predetermined step length, and a period in which the acceleration value is detected by the acceleration sensor 16. Since the change in altitude when the moving velocity of the electronic device 1c is slow is smaller than that when the moving velocity is fast, the atmospheric pressure sensor 17 does not need to detect the atmospheric pressure value frequently. Thus, the controller 19 changes the detection cycle of the atmospheric pressure sensor 17 based on the type of the moving state and the average moving velocity.

In this way, the electronic device 1c can suppress the power consumption by setting the detection cycle of the atmospheric pressure sensor 17 when the moving velocity is slow to be longer than that when the moving velocity is fast. The electronic device 1c can increase the detection sensitivity (accuracy) without decreasing the sensitivity of the atmospheric pressure sensor 17.

Figure 8:
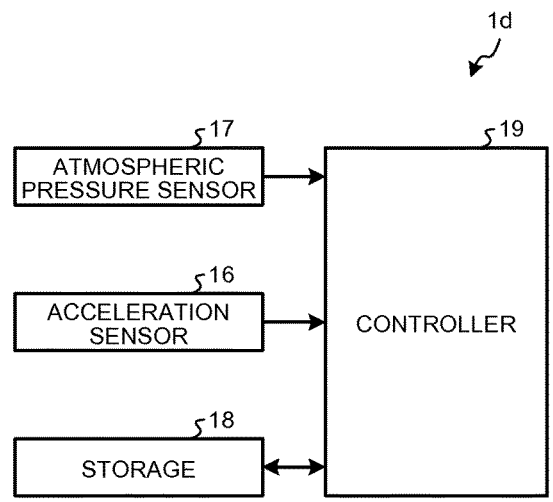
FIG. 8 is a block diagram illustrating a configuration of an electronic device according to an embodiment of some embodiments.

Another embodiment of an electronic device (mobile electronic device) according to the present disclosure and a system including the electronic device will be described. FIG. 8 is a block diagram illustrating a configuration of an electronic device 1d according to an embodiment.

Examples of the electronic device 1d include, but are not limited to, a mobile phone, a tablet computer, a pedometer, and a mobile game console. The electronic device 1d includes an atmospheric pressure sensor 17, an acceleration sensor 16, a storage 18, and a controller 19.

The atmospheric pressure sensor 17 detects an atmospheric pressure value. The electronic device 1d can detect an altitude or an altitudinal change since the atmospheric pressure sensor 17 detects the atmospheric pressure value.

The acceleration sensor 16 detects an acceleration value.

The controller 19 counts the number of steps based on the acceleration value detected by the acceleration sensor 16. The controller 19 counts the number of steps based on the amplitude or the like of the acceleration value detected by the acceleration sensor 16, for example. As a specific example, when conditions that a difference between the largest value and the smallest value in one cycle of an acceleration value is a predetermined difference or more and that a time difference between the largest value (smallest value) in one cycle of an acceleration value and the largest value (smallest value) in the next one cycle is a predetermined time difference or smaller are satisfied for a predetermined number of successive cycles, the controller 19 counts one cycle of the acceleration value as one step.

The controller 19 mitigates the conditions for counting the number of steps based on the atmospheric pressure value detected by the atmospheric pressure sensor 17 when a variation in atmospheric pressure value in relation to the number of steps is larger than a predetermined value. A variation in atmospheric pressure value in relation to the number of steps changes depending on the gradient of a road on which a person walks. The controller 19 may mitigate the conditions for counting the number of steps when a person moves on a road having a predetermined gradient or more. The controller 19 determines whether a person is moving on a road having a predetermined gradient or more based on a change in the atmospheric pressure value detected by the atmospheric pressure sensor 17 and a period in which the atmospheric pressure changes, for example.

For example, when a person climbs a slope or a mountain trail, the acceleration value (the largest and smallest amplitude values and the interval of the largest (smallest) amplitude values) detected by the acceleration sensor is likely to be unstable as compared to when a person walks on a level ground. This is because the attitude and the step length of a person climbing a slope or a mountain trail become unstable as compared to when a person walks on a level ground. Thus, if the number of steps of a person climbing a slope or a mountain trail is counted under the same conditions (settings) as a person walking on a level ground, it may be impossible to count the number of steps. Thus, when a person is climbing a slope or a mountain trail (when it is determined that the person is moving on a road having a predetermined gradient or more), the controller 19 mitigates the conditions for counting the number of steps as compared to when a person is walking on a level ground (the normal case) (when it is determined that the person is not moving on a road having a predetermined gradient or more). That is, the controller 19 mitigates the conditions so that the number of steps is counted even when a person is climbing a slope or a mountain trail. The conditions mitigated by the controller 19 include the conditions for counting the number of steps and the conditions for starting the counting of the number of steps.

In order to prevent detection errors, the conditions for counting the number of steps in a normal case are set in the following manner, for example. That is, the threshold of the cycle of the acceleration value is 1 [Hz (hertz)]. The threshold of the amplitude of the acceleration is 1000±100 [mg (milligram)]. The condition for successive walks is 10 steps.

On the other hand, the mitigated conditions for counting the number of steps are set as follows, for example. That is, the threshold of the cycle of the acceleration value is 0.5 [Hz (hertz)]. The threshold of the amplitude of the acceleration is 1000±50 [mg]). The condition for successive walks is five steps.

In this way, since the conditions for counting the number of steps are appropriately changed according to the state of a road surface on which a person is walking, the electronic device 1d can detect the waking state more accurately.

When it is determined that the user is not moving on a road having a predetermined gradient or more based on the atmospheric pressure value detected by the atmospheric pressure sensor 17, the controller 19 sets the cycle of the acceleration value detected by the acceleration sensor 16 to a first cycle. When the amplitude of the acceleration value detected based on the first cycle exceeds a first threshold and the number of times the amplitude successively exceeds the first threshold exceeds a first number of times, the controller 19 starts counting the number of steps. An example of the first cycle is 1 [Hz] as described above. An example of the first threshold is 1000±100 [mg] as described above. An example of the first number of times is 10 steps (10 times) as described above.

When it is determined that the user is moving on a road having a predetermined gradient or more based on the atmospheric pressure value detected by the atmospheric pressure sensor 17, the controller 19 sets the cycle of the acceleration value detected by the acceleration sensor 16 to a second cycle shorter than the first cycle. The controller 19 starts counting the number of steps by setting the first threshold to a second threshold smaller than the first threshold and setting the first number of times to a second number of times smaller than the first number of times. An example of the second cycle is 0.5 [Hz] as described above. An example of the second threshold is 1000±50 [mg] as described above. An example of the second number of times is five steps (five times) as described above.

Figure 9:
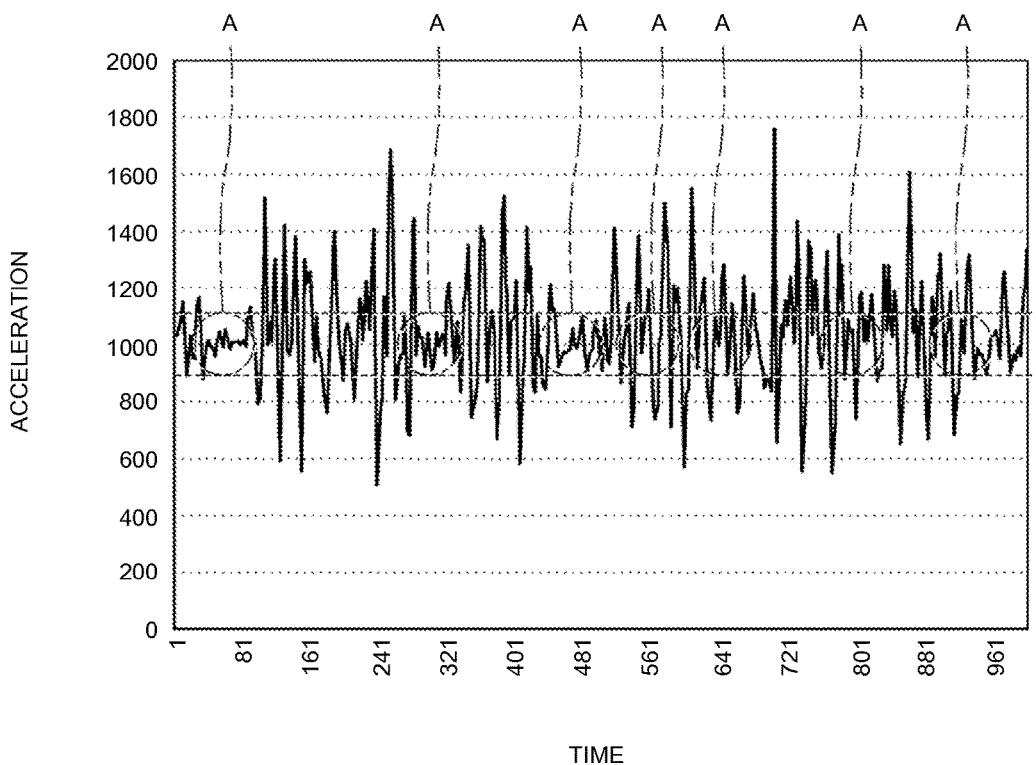
FIG. 9 is a diagram illustrating acceleration value detected by an acceleration sensor and a first threshold when a user moves on a road having a predetermined gradient or more according to an embodiment of some embodiments.
Figure 10:
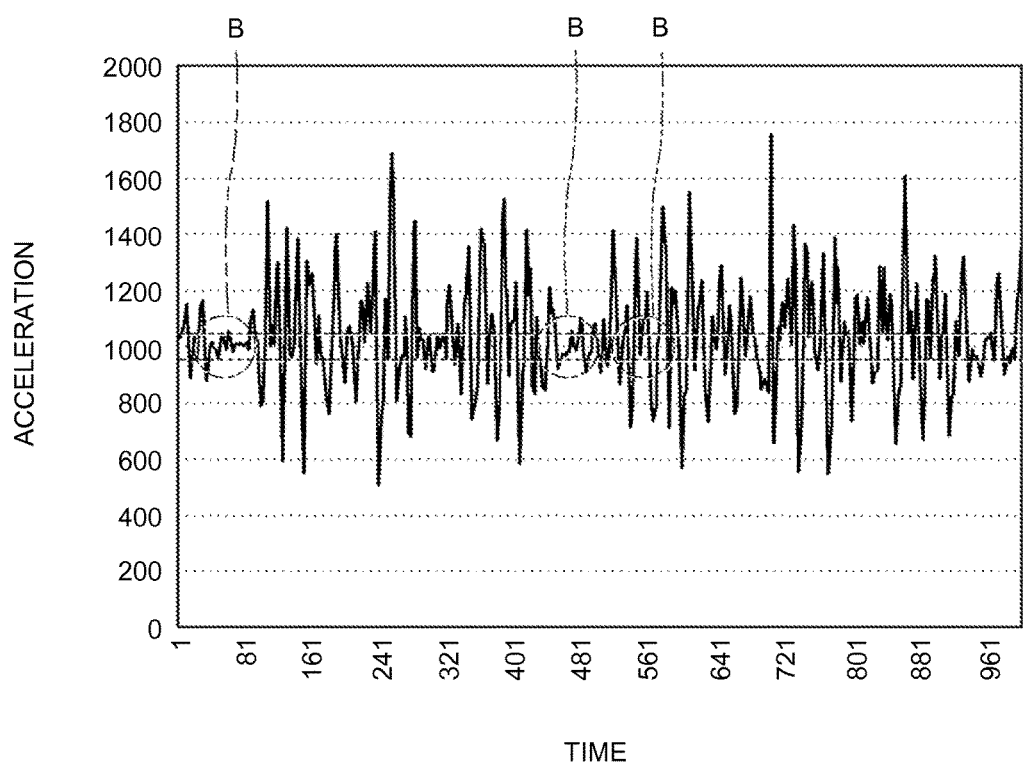
FIG. 10 is a diagram illustrating acceleration value detected by an acceleration sensor and a second threshold when a user moves on a road having a predetermined gradient or more according to an embodiment of some embodiments.

FIG. 9 is a diagram (illustrating a comparative example) illustrating the acceleration value detected by the acceleration sensor 16 and the first threshold when a person is moving on a road having a predetermined gradient or more. FIG. 10 is a diagram (illustrating an embodiment) illustrating the acceleration value detected by the acceleration sensor 16 and the second threshold when a person is moving on a road having a predetermined gradient or more.

When the first threshold is applied to a case in which a person is moving on a road having a predetermined gradient or more, there are a number of times the acceleration value does not exceed the first threshold as indicated by circles A in FIG. 9. That is, it is determined that the person is not walking in the portions indicated by circles A. Thus, in the case of FIG. 9, since there are a number of portions in which it is determined that the person is not walking, the counting of the number of steps is not started.

In contrast, when the second threshold is applied to a case in which a person is moving on a road having a predetermined gradient or more, there are a smaller number of times the acceleration value does not exceed the second threshold as indicated by circles B in FIG. 10 as compared to the case of FIG. 9. Thus, in the case of FIG. 10, it is possible to detect a larger number of walking states. In the case of FIG. 10, since the number of times is set to the second number of times smaller than the first number of times, it is possible to start counting the number of steps.

In this way, the electronic device 1d can count the number of steps since the conditions for counting the number of steps are appropriately changed according to the state of a road surface on which a person is walking.

When it is determined that the user is not moving on a road having a predetermined gradient or more based on the atmospheric pressure value detected by the atmospheric pressure sensor 17, the controller 19 may preferably add the first number of times to the counted number of steps. That is, when the amplitude of the acceleration value detected based on the first cycle exceeds the first threshold and the number of times the amplitude successively exceeds the first threshold exceeds the first number of times, the controller 19 sets the counted number of steps to 11 steps, for example, obtained by adding the first number of times rather than one step. In this case, the first number of times is 10 times.

When it is determined that the user is moving on a road having a predetermined gradient or more based on the atmospheric pressure value detected by the atmospheric pressure sensor 17, the controller 19 may preferably add the second number of times to the counted number of steps. That is, when the amplitude of the acceleration value detected based on the second cycle exceeds the second threshold and the number of times the amplitude successively exceeds the second threshold exceeds the second number of times, the counted number of steps is not one step but six steps, for example, obtained by adding the second number of times. In this case, the second number of times is five times.

In this way, the electronic device 1d can calculate the counted number of steps so as to match the actual number of steps a person has walked.

When there is a period in which it was not possible to count the number of steps based on the acceleration value detected by the acceleration sensor 16, the controller 19 may preferably store the atmospheric pressure value detected by the atmospheric pressure sensor 17 in the storage 18 together with the period. When it is determined that a person is moving on a road having a predetermined gradient or more based on the atmospheric pressure value stored in the storage 18, the controller 19 may preferably estimate the number of steps based on a period in which it was not possible to count the number of steps stored in the storage 18 and add the estimated number of steps to the counted number of steps.

In this case, the conditions are fixed at the first cycle, the first threshold, and the first number of times. For example, a person may walk on a level ground, then climb a slop, and then, walk on a level ground again. In this case, the acceleration value detected by the acceleration sensor 16 when the person climbs a slope may be less constant than when the person walks on a level ground. Thus, when the conditions are fixed at the first cycle, the first threshold, and the first number of times, there is a possibility that the number of steps when the person climbs a slope is not counted. Thus, when there is a period in which it was not possible to count the number of steps, the controller 19 stores the acceleration value and the atmospheric pressure value in that period in the storage 18.

The controller 19 reads the atmospheric pressure value stored in the storage 18 in a predetermined case and determines whether the person is moving on a road having a predetermined gradient or more based on the atmospheric pressure value. When it is determined that the person is moving on a road having the predetermined gradient or more, the controller 19 reads an acceleration value from the storage 18 and counts the number of steps in the period stored in the storage 18 based on the second cycle, the second threshold, and the second number of times. The controller 19 adds the number of steps counted in advance to the number of steps counted in the period stored in the storage 18. The predetermined case may be a case in which an operation of ending the counting of the number of steps is performed, for example.

In this way, the electronic device 1d can count the number of steps.

The electronic device 1d may have the following form. That is, the electronic device 1d includes an atmospheric pressure sensor 17, an acceleration sensor 16, a storage 18, and a controller 19.

The atmospheric pressure sensor 17 detects an atmospheric pressure value. The atmospheric pressure sensor 17 includes an atmospheric pressure sensor or a pressure sensor, for example. The electronic device 1d can detect an altitude or an altitudinal change since the atmospheric pressure sensor 17 detects the atmospheric pressure value.

The acceleration sensor 16 detects an acceleration value.

The controller 19 counts the number of steps based on the acceleration value detected by the acceleration sensor 16. The controller 19 counts the number of steps based on the amplitude or the like of the acceleration value detected by the acceleration sensor 16, for example. As a specific example, when conditions that a difference between the largest value and the smallest value in one cycle of an acceleration value is a predetermined difference or more and that a time difference between the largest value in one cycle of an acceleration value and the largest value in the next one cycle, or a time difference between the smallest value in one cycle of an acceleration value and the smallest value in the next one cycle is a predetermined time difference or smaller are satisfied for a predetermined number of successive cycles, the controller 19 counts one cycle of the acceleration value as one step.

When there is a period in which it was not possible to count the number of steps based on the acceleration value detected by the acceleration sensor 16, the controller 19 stores the atmospheric pressure value detected by the atmospheric pressure sensor 17 in the storage 18 together with the period. When it is determined that a person is moving on a road having a predetermined gradient or more based on the atmospheric pressure value stored in the storage 18, the controller 19 estimates the number of steps based on a period in which it was not possible to count the number of steps stored in the storage 18 and adds the estimated number of steps to the counted number of steps.

When a person walks on a slope, the acceleration value detected by the acceleration sensor 16 may fluctuate in a very small period due to a road pavement state, the user's fatigue level, or the like. Thus, the controller 19 sets the same conditions (conditions for counting the number of steps) for all walking states and counts the number of steps (first number of steps) based on the set conditions and the acceleration value detected by the acceleration sensor 16. Further, when there is a period in which the number of steps is not counted, the controller 19 stores the acceleration value detected by the acceleration sensor 16 and the atmospheric pressure value detected by the atmospheric pressure sensor 17 in that period in the storage 18. After that, the controller 19 reads the atmospheric pressure value stored in the storage 18 and determines whether the person is moving on a road having the predetermined gradient or more based on the atmospheric pressure value. When it is determined that the person is moving on a road having the predetermined gradient or more, the controller 19 mitigates the conditions for counting the number of steps, reads the acceleration value stored in the storage 18, and counts the number of steps (second number of steps) in the period stored in the storage 18 based on the mitigated conditions and the read acceleration value. The controller 19 adds the first number of steps and the second number of steps to acquire the number of steps in the entire period.

In this way, the electronic device 1d can count the number of steps.

The electronic device 1d described above can detect a walking state more accurately and count the number of steps. In this way, the electronic device 1d can obtain the calorie consumption or the like based on the counted number of steps, for example. That is, the electronic device 1d can obtain an accurate calorie consumption.

The invention claimed is:

1. An electronic device, comprising:
an acceleration sensor configured to detect an acceleration value;
an atmospheric pressure sensor configured to detect an atmospheric pressure value; and
a controller configured to calculate an amount of activity or a number of steps based on the acceleration value detected by the acceleration sensor and the atmospheric pressure value detected by the atmospheric pressure sensor, wherein
based on an acceleration signal detected by the acceleration sensor, the controller is configured to determine whether a change in an atmospheric pressure signal detected by the atmospheric pressure sensor results from an altitudinal change or an atmospheric pressure change,
when it is determined that the acceleration sensor is detecting an acceleration signal having a vibration amplitude larger than a second value,
the controller is configured to determine that the change in the atmospheric pressure signal detected by the atmospheric pressure sensor results from an altitudinal change, and
when it is determined that the acceleration sensor is detecting an acceleration signal having a vibration amplitude smaller than the second value but larger than a first value during a first period since the determination that the vibration amplitude of the acceleration signal is larger than the first value,
the controller is configured to determine that the change in the atmospheric pressure signal detected by the atmospheric pressure sensor results from an altitudinal change.

2. The electronic device according to claim 1, wherein the controller is configured to obtain the amount of activity based on the acceleration value and a difference in the atmospheric pressure values at a start and an end of movement.

3. The electronic device according to claim 2, wherein the controller is configured to obtain the amount of activity without based on the atmospheric pressure value when it is determined based on the acceleration value that a user of the electronic device moves by a bicycle and a type of the bicycle is set to a power-assisted bicycle.

4. The electronic device according to claim 1, wherein the controller is configured to:
determine an acceleration state based on the acceleration signal detected by the acceleration sensor, and
determine whether the change in the atmospheric pressure signal results from an altitudinal change or an atmospheric pressure change based on the determined acceleration state.

5. The electronic device according to claim 1, wherein the controller is configured to change a period in which the controller determines that the change in the atmospheric pressure signal detected by the atmospheric pressure sensor results from an altitudinal change based on an amplitude of the acceleration signal detected by the acceleration sensor.

6. A control method, comprising:
  detecting an acceleration value using an acceleration sensor;
  detecting an atmospheric pressure value using an atmospheric pressure sensor;
  based on an acceleration signal detected by the acceleration sensor, determining whether a change in an atmospheric pressure signal detected by the atmospheric pressure sensor results from an altitudinal change or an atmospheric pressure change; and
  calculating an amount of activity or a number of steps based on the detected acceleration value and the detected atmospheric pressure value, wherein
  said determining comprises
    when it is determined that the acceleration sensor is detecting an acceleration signal having a vibration amplitude larger than a second value,
      determining that the change in the atmospheric pressure signal detected by the atmospheric pressure sensor results from an altitudinal change, and
    when it is determined that the acceleration sensor is detecting an acceleration signal having a vibration amplitude smaller than the second value but larger than a first value during a first period since the determination that the vibration amplitude of the acceleration signal is larger than the first value,
      determining that the change in the atmospheric pressure signal detected by the atmospheric pressure sensor results from an altitudinal change.

7. A computer program product having computer instructions, stored on a non-transitory computer readable storage medium, for enabling an electronic device executing the computer instructions to perform operations comprising:
  detecting an acceleration value using an acceleration sensor;
  detecting an atmospheric pressure value using an atmospheric pressure sensor;
  based on an acceleration signal detected by the acceleration sensor, determining whether a change in an atmospheric pressure signal detected by the atmospheric pressure sensor results from an altitudinal change or an atmospheric pressure change; and
  calculating an amount of activity or a number of steps based on the detected acceleration value and the detected atmospheric pressure value, wherein
  said determining comprises
    when it is determined that the acceleration sensor is detecting an acceleration signal having a vibration amplitude larger than a second value,
      determining that the change in the atmospheric pressure signal detected by the atmospheric pressure sensor results from an altitudinal change, and
    when it is determined that the acceleration sensor is detecting an acceleration signal having a vibration amplitude smaller than the second value but larger than a first value during a first period since the determination that the vibration amplitude of the acceleration signal is larger than the first value,
      determining that the change in the atmospheric pressure signal detected by the atmospheric pressure sensor results from an altitudinal change.

\* \* \* \* \*